United States Patent
West et al.

(10) Patent No.: US 8,406,851 B2
(45) Date of Patent: Mar. 26, 2013

(54) PATIENT TRACKING USING A VIRTUAL IMAGE

(75) Inventors: Jay B. West, Mountain View, CA (US); Dongshan Fu, Santa Clara, CA (US)

(73) Assignee: Accuray Inc., Sunnyvale, CA (US)

( * ) Notice: Subject to any disclaimer, the term of this patent is extended or adjusted under 35 U.S.C. 154(b) by 1579 days.

(21) Appl. No.: 11/202,842

(22) Filed: Aug. 11, 2005

(65) Prior Publication Data
US 2007/0038058 A1 Feb. 15, 2007

(51) Int. Cl.
*A16B 5/005* (2006.01)
(52) U.S. Cl. ..................................... 600/411
(58) Field of Classification Search ............ 600/437, 600/439, 407, 417, 438, 461, 463, 464, 485; 382/128, 154, 294
See application file for complete search history.

(56) References Cited

U.S. PATENT DOCUMENTS

| | | | |
|---|---|---|---|
| 5,099,846 A | 3/1992 | Hardy | |
| 5,411,026 A | 5/1995 | Carol | |
| 5,633,951 A | 5/1997 | Moshfeghi | |
| 6,307,914 B1 | 10/2001 | Kunieda et al. | |
| 6,379,302 B1 * | 4/2002 | Kessman et al. | 600/437 |
| 6,650,927 B1 * | 11/2003 | Keidar | 600/424 |
| 6,740,883 B1 * | 5/2004 | Stodilka et al. | 250/363.04 |
| 6,754,374 B1 * | 6/2004 | Miller et al. | 382/128 |
| 2001/0029509 A1 * | 10/2001 | Smith et al. | 707/104.1 |
| 2001/0036302 A1 * | 11/2001 | Miller | 382/128 |
| 2003/0011624 A1 * | 1/2003 | Ellis | 345/646 |
| 2005/0101855 A1 * | 5/2005 | Miga et al. | 600/407 |
| 2005/0182319 A1 * | 8/2005 | Glossop | 600/424 |
| 2005/0288586 A1 * | 12/2005 | Ferek-Petric | 600/443 |
| 2007/0014448 A1 * | 1/2007 | Wheeler et al. | 382/128 |
| 2007/0019846 A1 * | 1/2007 | Bullitt et al. | 382/128 |
| 2007/0179377 A1 * | 8/2007 | Carlsen et al. | 600/407 |

OTHER PUBLICATIONS

PCT Preliminary Report on Patentability for PCT/US2006/027625, Int'l. filing date Jul. 14, 2006, Mailing date Feb. 21, 2008, (2 pgs.).
PCT Written Opinion of the International Searching Authority for PCT/US2006/027625, Int'l. filing date Jul. 14, 2006, Mailing date Feb. 21, 2008, (6 pgs.).
PCT International Search Report, PCT/US06/27625 filed Jul. 14, 2006, mailed Sep. 13, 2007.
PCT Written Opinion of the International Searching Authority, PCT/US06/27625 filed Jul. 14, 2006, mailed Sep. 13, 2007.
Coste-Manière, È., "Robotic whole body stereotactic radiosurgery: clinical advantages of the CyberKnife® integrated system", The International Journal of Medical Robotics +Computer Assisted Surgery, 2005, www.roboticpublications.com, pp. 28-39.
J. B. Antoine Maintz, Max A. Viergever, "A Surgey of Medical Image Registration", Medical Image Arrays (1998) vol. 2, No. 1, pp. 1-37.
A. Schweikard, H. Shiomi, J. Adler, "Respiration tracking in radiosurgery without fiducials", Int. J. Medical Robotics and Computer Assisted Surgery, 2005, 1(2): pp. 19-27.

* cited by examiner

*Primary Examiner* — Long V. Le
*Assistant Examiner* — Lawrence Laryea
(74) *Attorney, Agent, or Firm* — Lowenstein Sandler LLP

(57) ABSTRACT

An apparatus and method of tracking a patient using a virtual image.

16 Claims, 7 Drawing Sheets

PATIENT TRACKING USING A VIRTUAL IMAGE

TECHNICAL FIELD

Embodiments of the present invention pertain to the field of radiation treatment and, in particular, to patient tracking during radiation treatment.

BACKGROUND

Radiosurgery is a minimally invasive procedure that delivers high doses of ionizing radiation, in mono- or hypo-fractionated treatments, to destroy tumors or focal areas of pathology. The radiation dose has to optimally fit the tumor shape, while reducing the damage to collateral organs. The identification of the targeted lesion and its surrounding critical tissues is typically performed in a three-dimensional (3-D) space relative to the patient's reference frame during the pre-operative lesion identification phase. During the pre-operative planning phase, a conformal dose volume is sculpted around the target while minimizing the dose delivered to adjacent healthy tissues. This may be achieved using a combination of beam positions whose relative weights or dose contributions have been scaled to volumetrically shape the dose accordingly. In the model known as forward planning, the user manually specifies the desired weight of the various beams. The inverse planning method utilizes an algorithm to automatically calculate the optimum combination of beams and weights based on user-defined dose constraints to the target and healthy tissues.

Another method for tumor treatment is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source is changed, every beam passes through the tumor site, but passes through a different area of healthy tissue on its way to the tumor. As a result, the cumulative radiation dose at the tumor is high and the average radiation dose to healthy tissue is low. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centi-Gray (cGy)), short treatment times (e.g., 10 to 30 minutes per treatment) and hyper-fractionation (e.g., 30 to 45 days of treatment). For convenience, the term "radiation treatment" is used herein to mean radiosurgery and/or radiotherapy unless otherwise noted by the magnitude of the radiation.

During radiation treatment, a patient can change his or her position or orientation. In addition, pathological anatomies (e.g., tumor, legion, vascular malformation, etc.) may move during treatment, which decreases accurate target localization (i.e., accurate tracking of the position of the target). Most notably, soft tissue targets tend to move with patient breathing during radiosurgical treatment delivery sessions. Respiratory motion can move a tumor in the chest or abdomen, for example, by more than 3 centimeters (cm). In radiation treatment, accurate delivery of the radiation beams to the pathological anatomy being treated can be critical, in order to achieve the radiation dose distribution that was computed during the treatment planning stage.

One conventional solution for tracking motion of a target utilizes external markers (e.g., infrared emitters) placed on the outside of a patient (e.g., on the skin). The external markers are tracked automatically using an optical (e.g., infrared) tracking system. However, external markers cannot adequately reflect internal displacements caused by breathing motion. Large external patient motion may occur together with very small internal motion. For example, the internal target may move much slower than the skin surface.

Another conventional solution for tracking motion of a target involves the use of implanted fiducials. Typically, radiopaque fiducial markers (e.g., gold seeds or stainless steel screws) are implanted in close proximity to, or within, a target organ prior to treatment and used as reference points during treatment delivery. Stereo x-ray imaging is used during treatment to compute the precise spatial location of these fiducial markers (e.g., once every 10 seconds). However, internal markers alone may not be sufficient for accurate tracking. Furthermore, the tracking of internal fiducial markers can be difficult for the patient, because high accuracy tends to be achieved by using bone-implanted fiducial markers. The implanting of fiducial markers in bone requires a difficult and painful invasive procedure, especially for the C-spine, which may frequently lead to clinical complications. In addition, tracking bone-implanted fiducial markers may still may not provide accurate results for movement or deformation of soft tissue targets. Moreover, whether the fiducial marker is implanted in the bone or injected through a biopsy needle into soft tissue in the vicinity of the target area under computerized tomography (CT) monitoring, the patient must still undergo such invasive procedures before radiation treatment.

A conventional technique that tracks the motion of a tumor without the use of implanted fiducial markers is described in A. Schweikard, H Shiomi, J. Adler, Respiration Tracking in Radiosurgery Without Fiducials, Int J Medical Robotics and Computer Assisted Surgery, January 2005, 19-27. The described fiducial-less tracking technique use image registration methods. These methods may differ depending on the nature of the transformation involved. In particular, the transformation can be rigid or deformable. While rigid transformations (e.g., for head images) typically allow only translations and rotations, deformable transformations require solving a significantly more complex problem.

Image registration methods can be also divided into mono-modal (or intramodality) registration and multimodal (or intermodality) registration. In monomodal applications, the images to be registered belong to the same modality, as opposed to multimodal applications where the images to be registered stem from different modalities. Because of the high degree of similarity between the images of the same modality, solving the monomodal registration is usually an order of magnitude easier than in the multimodality applications, especially for deformable transformation.

An existing approach for measuring the patient position and orientation during radiation treatment involves registering projection X-rays taken during treatment with a pre-treatment CT scan. However, this approach is limited because X-rays cannot be taken frequently without additional radiation exposure to the patient. Furthermore, it is difficult to track soft tissue organs (e.g., lungs) on X-rays, without implanting fiducial markers in the vicinity of the target area.

BRIEF DESCRIPTION OF THE DRAWINGS

Embodiments of the present invention are illustrated by way of example, and not by way of limitation, in the figures of the accompanying drawings and in which.

DETAILED DESCRIPTION

In the following description, numerous specific details are set forth such as examples of specific components, devices, methods, etc., in order to provide a thorough understanding of the present embodiments. It will be apparent, however, to one skilled in the art that these specific details need not be employed to practice the present embodiments. In other instances, well-known materials or methods have not been described in detail in order to avoid unnecessarily obscuring the present embodiments.

The term "coupled to" as used herein may mean coupled directly to or indirectly to through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines, and each of the single signal lines may alternatively be buses. The terms "first," "second," "third," "fourth," etc. as used herein are meant as labels to distinguish among different elements and may not necessarily have an ordinal meaning according to their numerical designation.

Unless specifically stated otherwise as apparent from the following discussion, it is appreciated that throughout the description, discussions utilizing terms such as "processing" or "computing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices. Embodiments of the method described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the invention as described herein.

A method and system is described for tracking a patient during radiation treatment using a virtual image. The term "radiation treatment" is used herein to mean radiosurgery and/or radiotherapy unless otherwise noted by the magnitude of the radiation. The term "virtual image" used herein refers to an atlas, i.e., a pre-existing image of an arbitrary patient having substantially normal anatomy in terms of relative position and shape of structure or an averaged image of multiple patients.

During treatment planning, a required dose of radiation is determined using a pre-operative image (e.g., a computed tomography (CT) image, a magnetic resonance (MR) image, or fused MRI/CT). During treatment delivery, the current position of the patient is determined using an intra-operative image (e.g., an ultrasound (US) image, an MR image, etc.) of the patient. The intra-operative image and the pre-operative image may be of two different types. For example, the pre-operative image may be a CT image and the intra-operative image may a US image. Deformable registration of such different images creates a difficult problem. Embodiments of the present invention overcome this difficulty by performing a series of deformable registrations using an atlas. The atlas may be, for example, a CT atlas with ultrasound information drawn onto it, so that every position in the CT atlas has corresponding ultrasound intensity. The registration between the pre-operative CT image and the intra-operative US image may be performed, in one embodiment, by first registering the CT image with the CT atlas using CT data in the atlas, and then registering ultrasound data on the atlas with the US image, thus tracking the patient position. In an alternative embodiment, the registration may be performed by first registering the US image with the atlas using ultrasound data on the atlas, and then registering the atlas with the CT image using CT data on the atlas.

Figure 1:
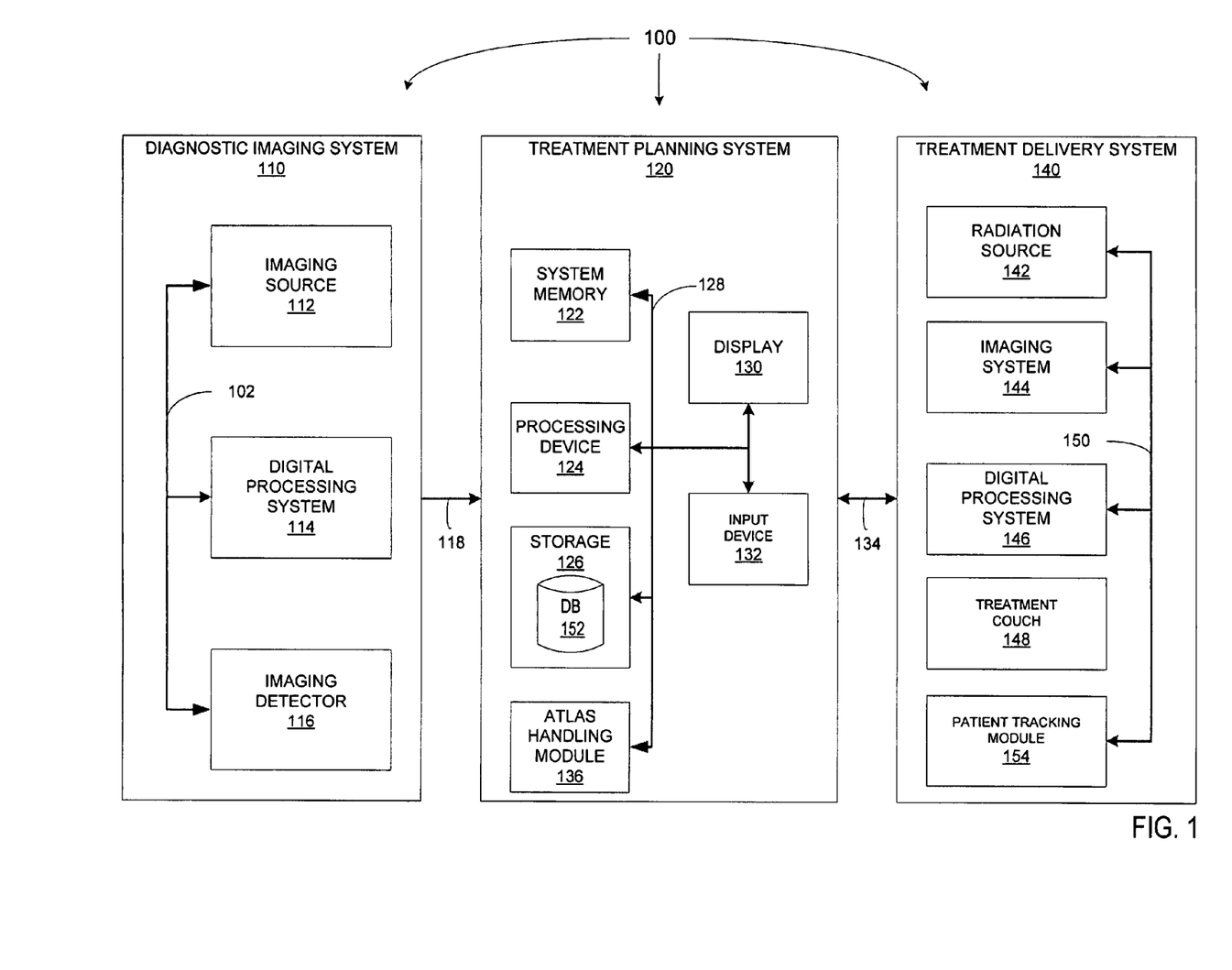
FIG. 1 illustrates one embodiment of systems that may be used in performing radiation treatment in which features of the present invention may be implemented.

FIG. 1 illustrates one embodiment of systems that may be used in performing radiation treatment in which features of the present invention may be implemented. As described below and illustrated in FIG. 1, systems 100 may include a diagnostic imaging system 110, a treatment planning system 120 and a treatment delivery system 140.

Diagnostic imaging system 110 may be any system capable of producing medical diagnostic images of a volume of interest (VOI) in a patient that may be used for subsequent medical diagnosis, treatment planning and/or treatment delivery. For example, diagnostic imaging system 110 may be a computed tomography (CT) system, a magnetic resonance imaging (MRI) system, a positron emission tomography (PET) system, an ultrasound system or the like. For ease of discussion, diagnostic imaging system 110 may be discussed below at times in relation to a CT imaging modality. However, other imaging modalities such as those above may also be used.

Diagnostic imaging system 110 includes an imaging source 112 to generate an imaging beam (e.g., x-rays, ultrasonic waves, radio frequency waves, etc.) and an imaging detector 116 to detect and receive the beam generated by imaging source 112, or a secondary beam or emission stimulated by the beam from the imaging source (e.g., in an MRI or PET scan). In one embodiment, diagnostic imaging system 110 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, can also be used that would be illuminated by each x-ray imaging source. Alternatively, other numbers and configurations of imaging sources and imaging detectors may be used.

The imaging source 112 and the imaging detector 116 are coupled to a digital processing system 114 to control the imaging operation and process image data. Diagnostic imaging system 110 includes a bus or other means 102 for transferring data and commands among digital processing system 114, imaging source 112 and imaging detector 116. Digital processing system 114 may include one or more general-purpose processors (e.g., a microprocessor), special purpose processor such as a digital signal processor (DSP) or other type of device such as a controller or field programmable gate array (FPGA). Digital processing system 114 may also include other components (not shown) such as memory, storage devices, network adapters and the like. Digital processing system 114 may be configured to generate digital diagnostic images in a standard format, such as the DICOM (Digital Imaging and Communications in Medicine) format, for example. In other embodiments, digital processing system 114 may generate other standard or non-standard digital image formats. Digital processing system 114 may transmit diagnostic image files (e.g., the aforementioned DICOM formatted files) to treatment planning system 120 over a data link 118, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 120 includes a processing device 124 to receive and process image data. Processing device 124 may represent one or more general-purpose processors (e.g., a microprocessor), special purpose processor such as a digital signal processor (DSP) or other type of device such as a controller or field programmable gate array (FPGA). Processing device 124 may be configured to execute instructions for performing treatment planning operations discussed herein.

Treatment planning system 120 may also include system memory 122 that may include a random access memory (RAM), or other dynamic storage devices, coupled to processing device 124 by bus 128, for storing information and instructions to be executed by processing device 124. System memory 122 also may be used for storing temporary variables or other intermediate information during execution of instructions by processing device 124. System memory 122 may also include a read only memory (ROM) and/or other static storage device coupled to bus 128 for storing static information and instructions for processing device 124.

Processing device 124 may also be coupled to a display device 130, such as a cathode ray tube (CRT) or liquid crystal display (LCD), for displaying information (e.g., a 2D or 3D representation of the VOI) to the user. An input device 132, such as a keyboard, may be coupled to processing device 124 for communicating information and/or command selections to processing device 124. One or more other user input devices (e.g., a mouse, a trackball or cursor direction keys) may also be used to communicate directional information, to select commands for processing device 124 and to control cursor movements on display 130.

Treatment planning system 120 may also include storage device 126, representing one or more storage devices (e.g., a magnetic disk drive or optical disk drive) coupled to bus 128 for storing information and instructions. Storage device 126 may be used for storing instructions for performing the treatment planning operations discussed herein.

In one embodiment, storage device 126 includes a database 152 that stores 3D images of patients obtained by the diagnostic imaging system 110 prior to treatment. These images may be, for example, CT images of patients or MR images of patients. The treatment planning system may use these images for radiation dose calculation and/or other treatment planning operations discussed herein.

In one embodiment, the treatment planning system 120 includes an atlas handling module 136 to prepare one or more atlases for future use by the treatment planning system 120 during delivery of treatment, as will be discussed in more detail below. In one embodiment, the atlas handling module 136 resides in memory 122 and contains processing logic for execution by the processing device 124. In another embodiment, the atlas handling module 136 contains processing logic that comprises hardware such as circuitry, dedicated logic, programmable, logic, microcode, etc. In yet another embodiment, the atlas handling module 136 contains processing logic that comprises a combination of software and hardware.

It will be appreciated that treatment planning system 120 represents only one example of a treatment planning system, which may have many different configurations and architectures, which may include more components or fewer components than treatment planning system 120 and which may be employed with the present invention. For example, some systems often have multiple buses, such as a peripheral bus, a dedicated cache bus, etc. The treatment planning system 120 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.).

Treatment planning system 120 may share its database 152 with a treatment delivery system, such as treatment delivery system 140, so that it may not be necessary to export from the treatment planning system prior to treatment delivery. Treatment planning system 120 may be linked to treatment delivery system 140 via a data link 134, which may be a direct link, a LAN link or a WAN link as discussed above with respect to data link 118. It should be noted that when data links 118 and 134 are implemented as LAN or WAN connections, any of diagnostic imaging system 110, treatment planning system 120 and/or treatment delivery system 140 may be in decentralized locations such that the systems may be physically remote from each other. Alternatively, any of diagnostic imaging system 110, treatment planning system 120 and/or treatment delivery system 140 may be integrated with each other in one or more systems.

Treatment delivery system 140 includes a therapeutic and/or surgical radiation source 142 to administer a prescribed radiation dose to a target volume in conformance with a treatment plan. Treatment delivery system 140 may also include an imaging system 144 to capture intra-treatment images of a patient volume (including the target volume) for registration or correlation with the diagnostic images described above in order to position the patient with respect to the radiation source. Treatment delivery system 140 may also include a digital processing system 146 to control radiation source 142, imaging system 144, and a patient support device such as a treatment couch 148. Digital processing system 146 may include one or more general-purpose processors (e.g., a microprocessor), special purpose processor such as a digital signal processor (DSP) or other type of device such as a controller or field programmable gate array (FPGA). Digital processing system 146 may also include other components (not shown) such as memory, storage devices, network adapters and the like. Digital processing system 146 may be coupled to radiation source 142, imaging system 144 and treatment couch 148 by a bus 150 or other type of control and communication interface.

In one embodiment, the treatment delivery system 120 includes a patient tracking module 154 to track the patient position and orientation during treatment delivery. As will be discussed in more detail below, the patient tracking module 154 may track the patient using one or more atlases prepared by the atlas handling module 136 and stored in the database 152. In one embodiment, the patient tracking module 154 resides in memory of the digital processing system 146 and contains processing logic that is run on the digital processing system 146. In another embodiment, the patient tracking module 154 contains processing logic that comprises hardware such as circuitry, dedicated logic, programmable, logic, microcode, etc. In yet another embodiment, the patient tracking module 154 contains processing logic that comprises a combination of software and hardware.

Figure 2:
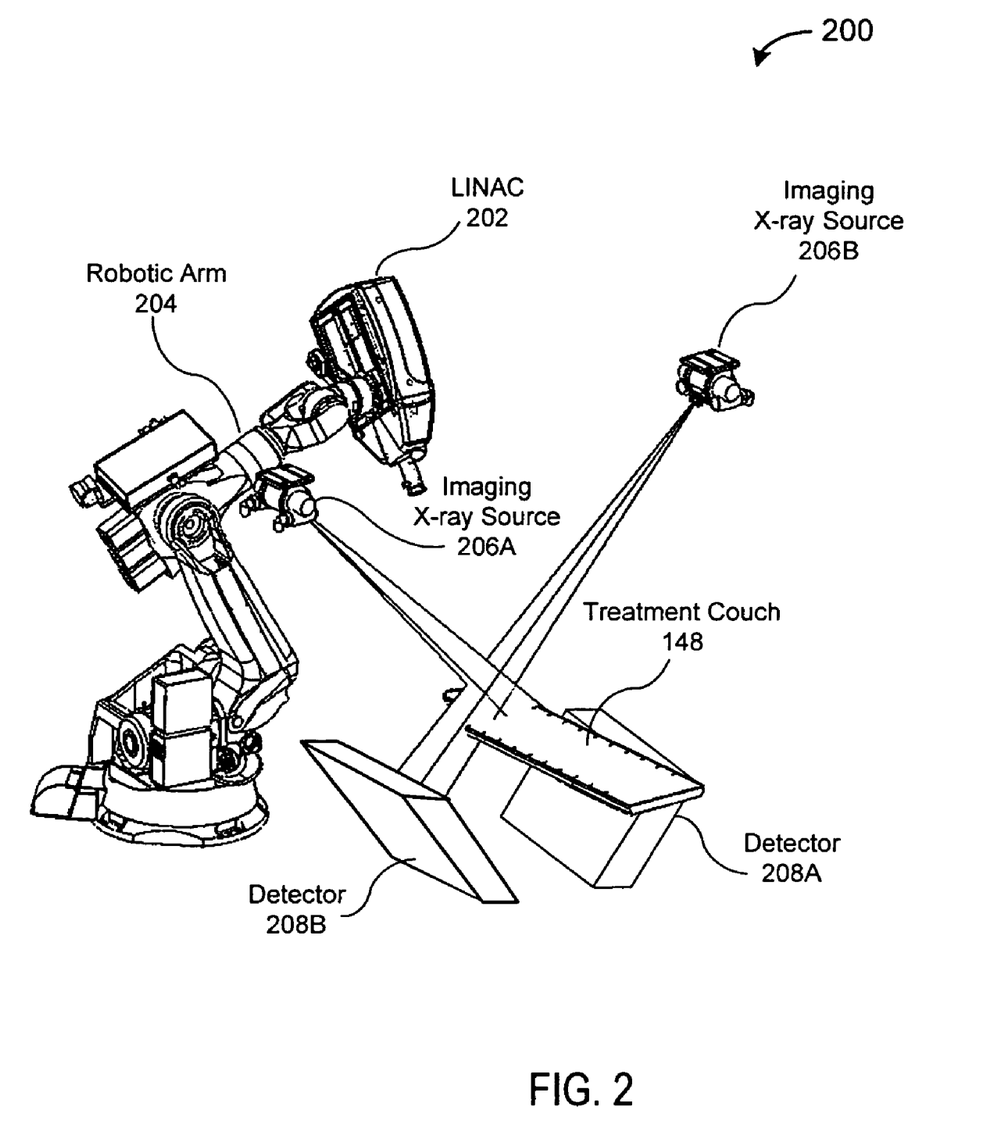
FIG. 2 illustrates one embodiment of an image-guided, robotic-based radiation treatment system.

In one embodiment, as illustrated in FIG. 2, treatment delivery system 140 may be an image-guided, robotic-based radiation treatment system 200 (e.g., for performing radiosurgery) such as the CyberKnife® system developed by Accuray, Inc. of California. In FIG. 2, radiation source 142 may be represented by a linear accelerator (LINAC) 202 mounted on the end of a robotic arm 204 having multiple (e.g., 5 or more) degrees of freedom in order to position the LINAC 202 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions (hypo-fractionation) as determined during treatment planning. With treatment delivery system 200, in one embodiment, radiation beams may be delivered according to the treatment plan without fixing the patient to a rigid, external frame to register the intra-operative position of the target volume with the position of the target volume during the pre-operative treatment planning phase.

In FIG. 2, imaging system 144 may be represented by X-ray sources 206A and 206B and X-ray image detectors (imagers) 208A and 208B. In one embodiment, for example, two x-ray sources 206A and 206B may be nominally aligned to project imaging x-ray beams through a patient from two different angular positions (e.g., separated by 90 degrees, 45 degrees, etc.) and aimed through the patient on treatment couch 148 toward respective detectors 208A and 208B. In another embodiment, a single large detector can be used that would be illuminated by each x-ray imaging source. Alternatively, other numbers and configurations of imaging sources and detectors may be used.

Digital processing system 146 may implement algorithms to register images obtained from imaging system 144 with pre-operative treatment planning images in order to align the patient on the treatment couch 148 within the treatment delivery system 200, and to precisely position the radiation source with respect to the target volume.

The treatment couch 148 may be coupled to another robotic arm (not illustrated) having multiple (e.g., 5 or more) degrees of freedom. The couch arm may have five rotational and translational degrees of freedom and one substantially vertical, linear degree of freedom. Alternatively, the couch arm may have six rotational and translational degrees of freedom and one substantially vertical, linear degree of freedom or at least four rotational and translational degrees of freedom. The couch arm may be vertically mounted to a column or wall, or horizontally mounted to pedestal, floor, or ceiling. Alternatively, the treatment couch 148 may be a component of another mechanical mechanism, such as the Axum® treatment couch developed by Accuray, Inc. of California, or be another type of conventional treatment table known to those of ordinary skill in the art.

Alternatively, treatment delivery system 200 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

In other embodiments, yet another type of treatment delivery system 200 may be used, for example, a stereotactic frame system such as the GammaKnife®, available from Elekta of Sweden. With such a system, the optimization algorithm (also referred to as a sphere packing algorithm) of the treatment plan determines the selection and dose weighting assigned to a group of beams forming isocenters in order to best meet provided dose constraints.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

Referring again to FIG. 1, as discussed above, the treatment planning system 120 may include an atlas handling module 136 to prepare one or more atlases for future use by the treatment delivery system 140. The atlases may include an atlas of a pre-operative imaging modality (e.g., a CT atlas) and a corresponding atlas of an intra-operative imaging modality (e.g., an ultrasound atlas). For example, the CT and ultrasound atlas may be created by first performing a calibration step in which the coordinate space of the CT scan is calibrated with respect to that of the ultrasound scan. One method of doing this may be to perform a CT and ultrasound scan of a phantom containing fiducial points of known geometry that are visible in both CT and ultrasound. Another method may be to mount the ultrasound scanner in a known orientation and position with respect to the CT scanner. Next, for example, the diagnostic imaging system 110 may perform a CT scan of an arbitrary patient to produce a CT atlas, and then an ultrasound scan of the same patient, without any movement of the patient, to produce an ultrasound atlas. Alternatively, the diagnostic imaging system 110 may perform an ultrasound scan of an arbitrary patient to produce an ultrasound atlas, and then a CT scan of the same patient, without any movement of the patient, to produce a CT atlas. In one embodiment, the atlas handling module 136 stores both atlases in the database 152 for future use by the treatment delivery system 140.

In another embodiment, the atlas handling module 136 creates a combined atlas from the two atlases described above and stores the combined atlas in the database 152 for future use by the treatment delivery system 140. In one embodiment, the atlas handling module 136 creates a combined atlas by overlaying the first atlas with the second atlas. For example, the atlas handling module 136 may map ultrasound data from the ultrasound atlas to CT data on the CT atlas, and then add the ultrasound data to the CT atlas based on the mapping. Alternatively, the atlas handling module 136 may map CT data from the CT atlas to ultrasound data on the ultrasound atlas, and then add the CT data to the ultrasound atlas based on the mapping. In other embodiments, the atlas handling module 136 may create a combined atlas in other manners, such as by acquiring the two atlases in the same space (e.g., using a CT/ultrasound scanner) or by registering the first atlas with the second atlas using techniques known in the art.

In another embodiment, the atlas handling module 136 uses a single atlas to create a combined atlas. For example, the atlas handling module 136 may select a CT atlas (e.g., a CT image of an arbitrary patient) from CT images stored in the database 152. Then, anatomical organs may be delineated on the CT atlas. The delineation may be performed manually, or may be aided by automated segmentation tools such as intensity-based methods, shape-based methods, or both. Next, Ultrasound intensities may be added to the atlas. The ultrasound intensity for each organ may be determined manually by the user, or may be taken from a table stored in the database giving typical ultrasound intensity distributions for anatomical organs. Alternatively, the atlas handling module 136 may select an ultrasound atlas (e.g., an ultrasound image of an arbitrary patient) from ultrasound images stored in the database 152, determine corresponding CT data for the positions in the ultrasound atlas using methods described above, and then add these corresponding CT data to the ultrasound atlas. The initial atlas (e.g., a CT atlas or ultrasound atlas) may be selected based on patient parameters provided by the user (e.g., parameters for a patient with substantially normal anatomy in terms of relative position and shape of structure). Alternatively, an initial atlas may be created by selecting images of multiple patients and composing them into a single image pertaining to an average patient.

In one embodiment, the combined atlas is created once and is used for different patients. In another embodiment, the combined atlas may be created for each patient. In yet another embodiment, the combined atlas may be re-created prior to each treatment delivery.

As discussed above, in one embodiment, the atlas handling module 136 stores the combined atlas in the database 152 for future use by the treatment delivery system 140. In an alternative embodiment, the atlas handling module 136 performs additional processing with respect to the combined atlas to simplify computations during future treatment delivery. In particular, in one embodiment, the atlas handling module 136 performs a deformable registration of a pre-operative modality image (e.g., a CT image used for radiation dose calculation) with the combined atlas using the pre-operative modality data (e.g., CT data) on the combined atlas. Data involved in this registration is associated with the same modality, and, therefore, this registration is not computationally intense. The result of this registration is the combined atlas deformed to match the pre-operative modality data (e.g., CT data) on the atlas with the pre-operative modality image (e.g., CT image).

The atlas handling module 136 then stores the deformed atlas in the database 152 for future use by the treatment delivery system 140.

As discussed above, the treatment delivery system 140 may include the patient tracking module 154 for tracking the patient position and orientation during treatment delivery. Small changes may be accommodated by adjusting the parameters of the radiation source. Larger changes may necessitate a pause in treatment while the patient is repositioned.

The patient tracking module 154 makes measurements of the patient position and orientation by registering images obtained during treatment with a pre-treatment image (e.g., a pre-operative CT scan) that was used for treatment planning. The intra-operative images are obtained by the imaging system 144 using an imaging modality that does not require additional exposure of the patient to radiation. Such a modality may be, for example, an ultrasound scan or an MR scan. In one embodiment, a pre-operative modality and an intra-operative modality are of two different types (e.g., a pre-operative CT scan and an intra-operative ultrasound scan). Then, deformable registration may present a difficult problem. The patient tracking module 154 solves this problem using a virtual image. In particular, in one embodiment, the patient tracking module 154 uses an atlas processed by the treatment planning system 120 and stored in the database 152. In one embodiment, this atlas is a combined atlas that contains data of a pre-operative modality and data of an intra-operative modality. The combined atlas may be, for example, a CT atlas with ultrasound information drawn onto it, so that every position in the CT atlas has a corresponding ultrasound intensity. Alternatively, this atlas may be an ultrasound atlas with corresponding CT information drawn onto it. In another embodiment, the patient tracking module 154 retrieves two atlases (e.g., a CT atlas and an ultrasound atlas) from the database 152 and creates a combined atlas in a manner discussed above.

In one embodiment, the patient tracking module 154 registers a pre-operative image with an intra-operative image by performing a series of deformable registrations. In particular, the patient tracking module 154 first performs a deformable registration of the pre-operative image with the combined atlas using pre-operative data on the atlas, and then performs a deformable registration of the combined atlas with the intra-operative image using intra-operative data on the atlas. These deformable registrations are intra-modality registrations and, therefore, do not involve extensive computations. The resulting deformed intra-operative image indicates changes in the patient position and orientation, as compared to the patient's position and orientation at the time the pre-operative image was acquired.

In another embodiment, the registration of the pre-operative image with the combined atlas is performed prior to treatment by the treatment planning system 120 which stores the resulting deformed atlas in the shared database 152, as discussed above. Then, the patient tracking module 154 retrieves the deformed atlas from the database 152, and then registers this atlas with the intra-operative image using intra-operative data on the atlas.

In yet another embodiment, the patient tracking module 154 performs a series of deformable registrations in a reversed order by first registering the intra-operative image with the combined atlas using intra-operative data on the atlas, and then registering the combined atlas with the pre-operative image. The resulting deformed pre-operative image then indicates changes in the patient position and orientation.

Figure 3:
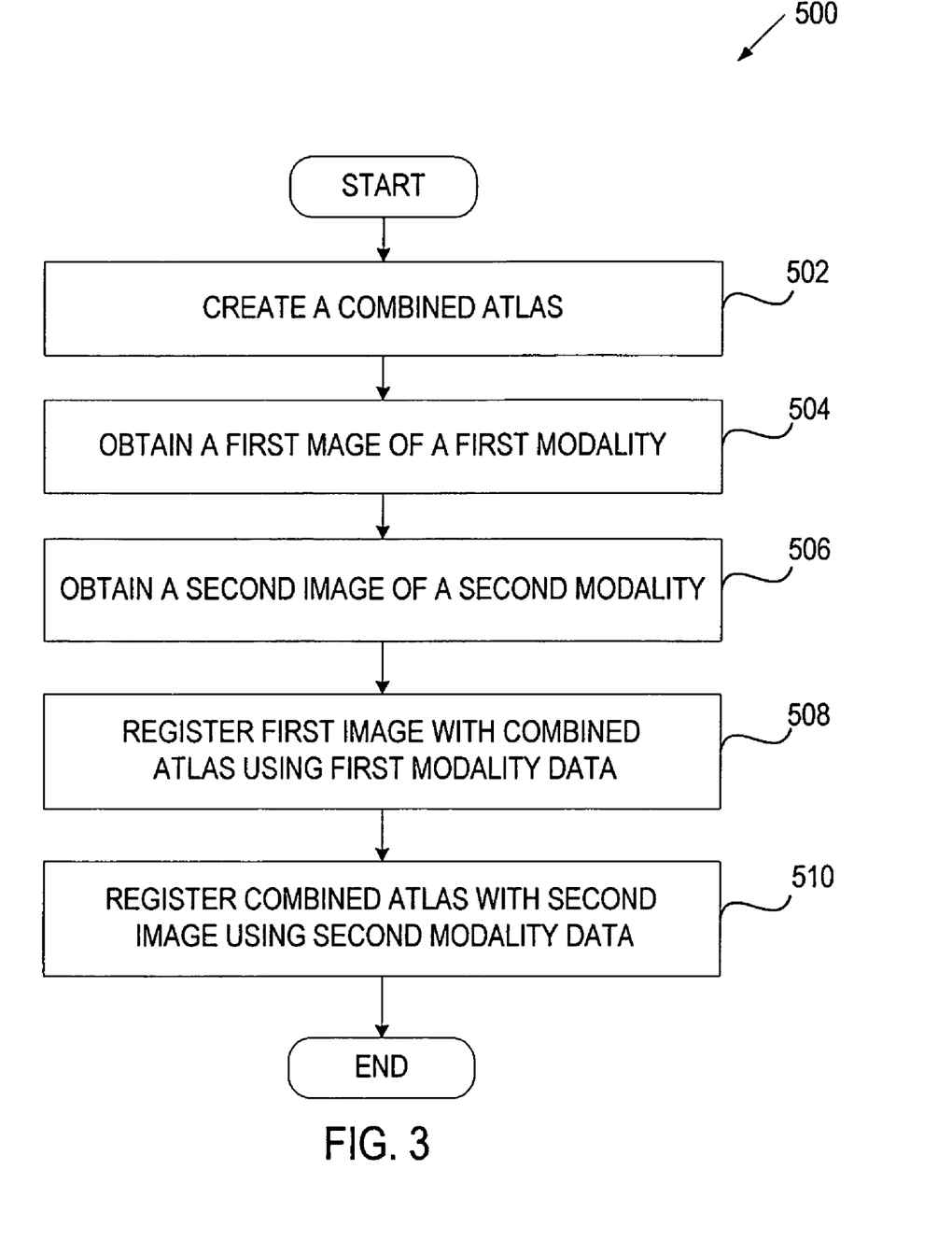
FIG. 3 is a flow diagram of one embodiment of a process for registering images of different modality types.

FIG. 3 is a flow diagram of one embodiment of a process 500 for deformably registering images of different imaging modality types. The process may be performed by processing logic of the atlas handling module 136 and/or processing logic of the patient tracking module 154. Processing logic may comprise hardware (e.g., circuitry, dedicated logic, programmable logic, microcode, etc.), software (such as run on a general purpose computer system or a dedicated machine), or a combination of both.

Referring to FIG. 3, processing logic begins with processing logic creating a combined atlas from two atlases of different modalities (e.g., a CT atlas and an ultrasound atlas) (processing block 502). In one embodiment, processing logic creates the combined atlas by mapping data from the first atlas to data in the second atlas, and then superimposing first modality data from the first atlas on the second atlas using the mapping. For example, processing logic may map ultrasound data from the ultrasound atlas to CT data on the CT atlas, and then add the ultrasound data to the CT atlas based on the mapping. Alternatively, processing logic may create a combined atlas by selecting a first modality image of an arbitrary patient, automatically determining second modality data corresponding to the first modality data in the image, and adding the second modality data to the first modality image.

In one embodiment, the combined atlas is created once and is used for all patients. In another embodiment, the combined atlas may be created for each patient. In yet another embodiment, the combined atlas may be re-created prior to each treatment delivery.

At processing block 504, processing logic obtains a first modality image (e.g., a CT image) of the patient. In one embodiment, the first modality image is retrieved from the database 152 to develop a treatment plan before treatment delivery.

At processing block 506, processing logic obtains a second modality image (e.g., an ultrasound image) of the patient. The first and second modalities are of two different types. In one embodiment, the second modality image is obtained during treatment delivery.

Next, processing logic registers the first modality image with the second modality image using a series of deformable registrations. In particular, at processing block 508, processing logic performs a deformable registration of the first modality image with the combined atlas using first modality data on the combined atlas. In one embodiment, this deformable registration is performed prior to treatment delivery. Alternatively, it is performed during treatment delivery.

At processing block 510, processing logic performs a deformable registration of the combined atlas deformed at processing block 508 with the second modality image. Each of these deformable registrations involves an intra-modality transformation that does not require intensive computations. The resulting second modality image deformed to match the combined atlas indicates changes in the patient position and orientation.

In one embodiment, the first modality image is a pre-operative CT image and the second modality image is an intra-operative ultrasound image, and the registration process is divided into two stages: a treatment planning stage and a treatment delivery stage.

Figure 4:
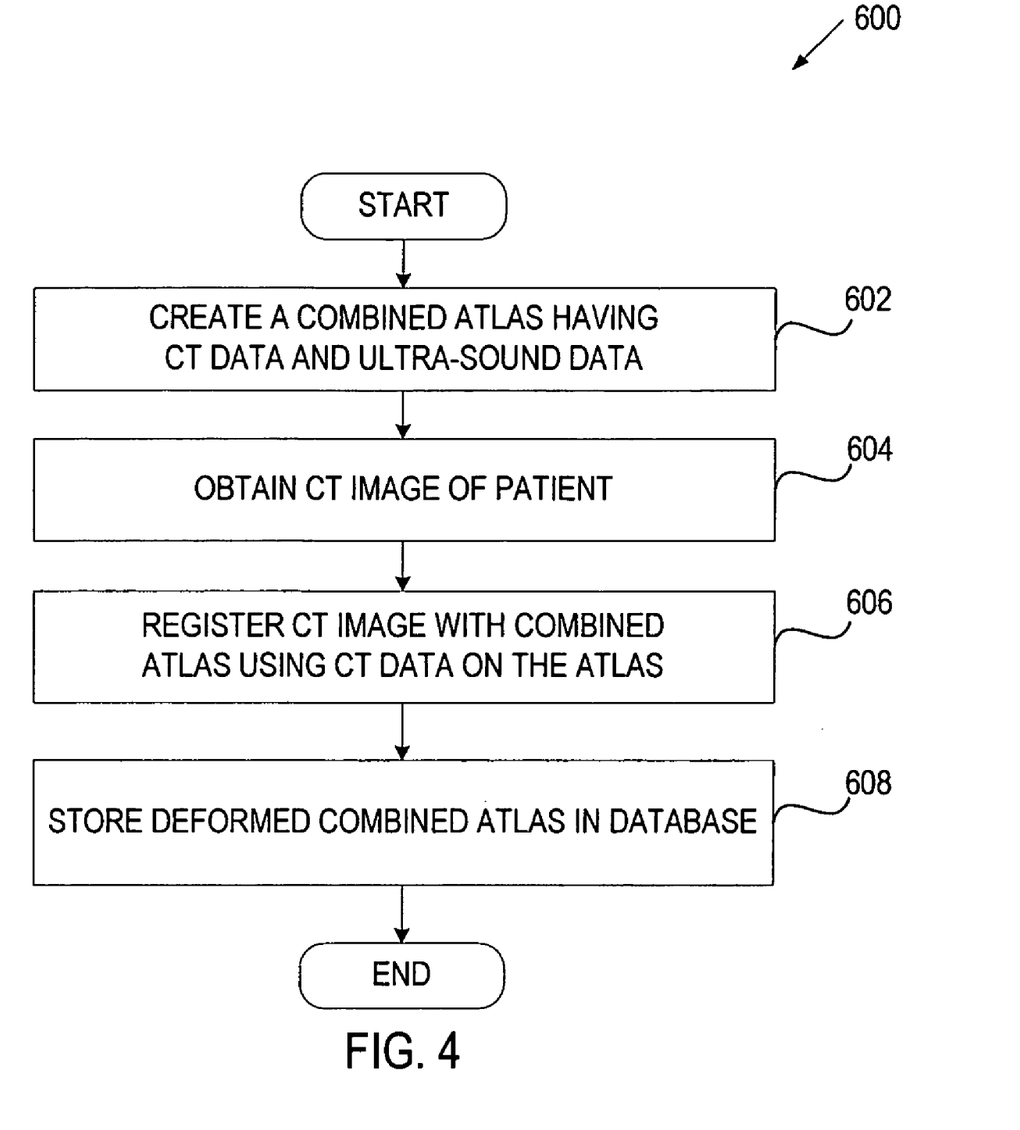
FIG. 4 is a flow diagram of one embodiment of a process for performing a treatment planning stage of image registration.

FIG. 4 is a flow diagram of one embodiment of a process 600 for performing a treatment planning stage of image registration. The process may be performed by processing logic of the atlas handling module 136. Processing logic may comprise hardware (e.g., circuitry, dedicated logic, programmable logic, microcode, etc.), software (such as run on a general purpose computer system or a dedicated machine), or a combination of both.

Referring to FIG. 4, process 600 begins with processing logic creating a combined atlas having CT data and ultrasound data (processing block 602). In one embodiment, the combined atlas is a CT atlas having ultrasound data drawn onto it, so that every position in the CT atlas has a corresponding ultrasound intensity. Alternatively, the combined atlas is an ultrasound atlas having corresponding CT data drawn onto it.

At processing block 604, processing logic obtains a CT image of the patient. The CT image may be obtained to identify the target and calculate the radiation dose.

At processing block 606, processing logic performs a deformable registration of the CT image with the combined atlas using the CT data on the atlas.

At processing block 608, processing logic stores the combined atlas deformed at processing block 606 in a database.

Figure 5:
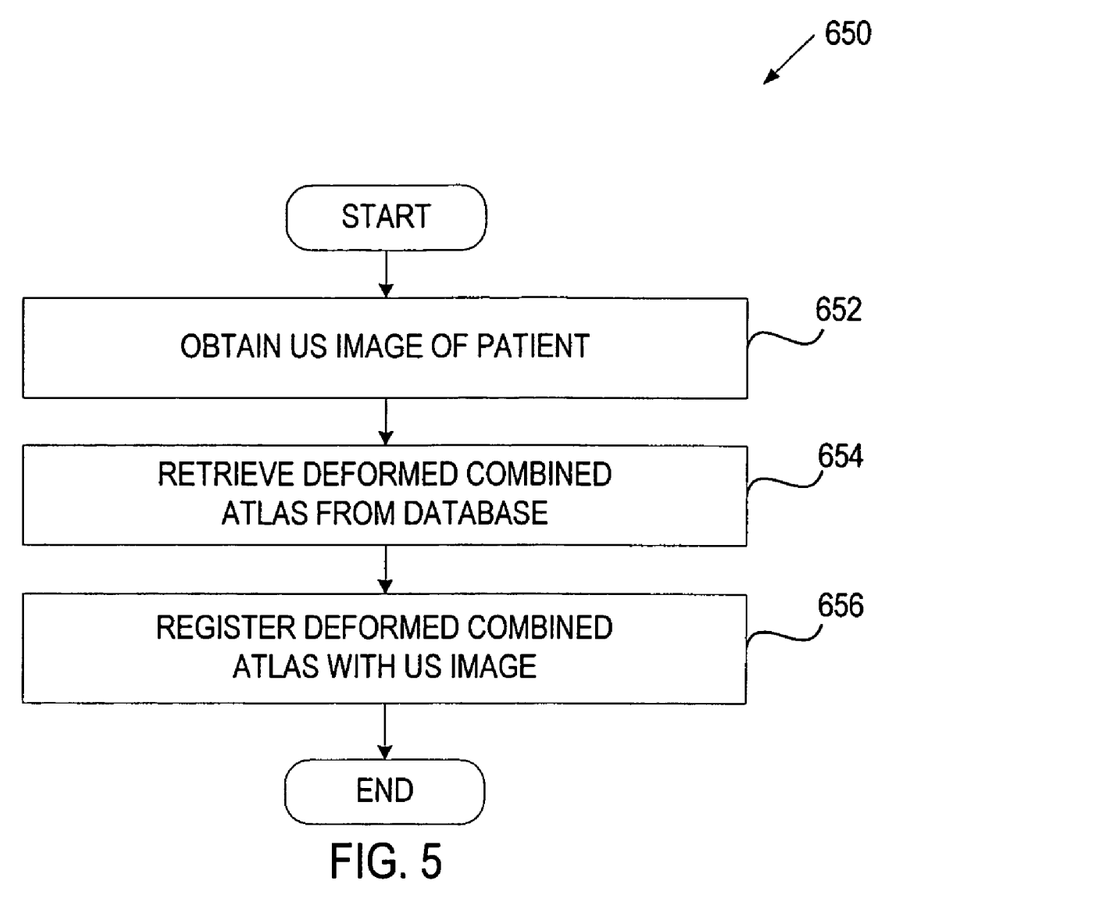
FIG. 5 is a flow diagram of one embodiment of a process for performing a treatment delivery stage of image registration.

FIG. 5 is a flow diagram of one embodiment of a process 650 for performing a treatment delivery stage of image registration. The process may be performed by processing logic of the patient tracking module 154. Processing logic may comprise hardware (e.g., circuitry, dedicated logic, programmable logic, microcode, etc.), software (such as run on a general purpose computer system or a dedicated machine), or a combination of both.

Referring to FIG. 5, process 650 begins with processing logic obtaining an ultrasound image of the patient during treatment delivery (processing block 652).

At processing block 654, processing logic retrieves from the database the combined atlas that was previously deformed to match the pre-operative CT image.

At processing block 656, processing logic performs a deformable registration of the retrieved atlas with the ultrasound image using ultrasound data on the atlas. The ultrasound image deformed to match the ultrasound data on the atlas indicates changes in the patient position and orientation.

Figure 6:
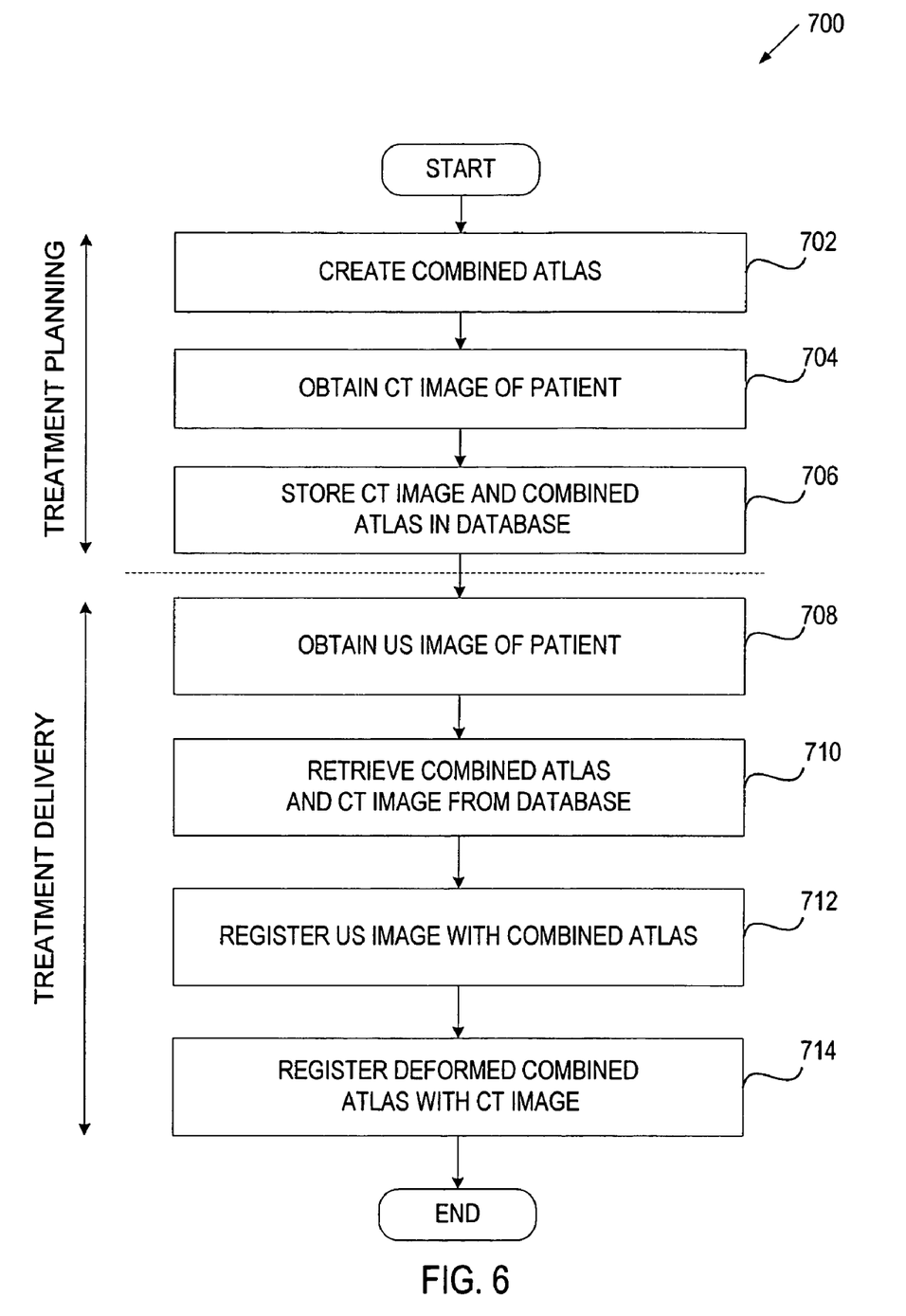
FIG. 6 is a flow diagram of an alternative embodiment of a process for registering images of different modality types.

In an alternative embodiment, a series of deformable registrations may be performed in a reversed order. FIG. 6 is a flow diagram of an alternative embodiment of a process 700 for deformably registering images of different modality types. The process may be performed by processing logic of atlas handling module 136 and processing logic of patient tracking module 154. Processing logic may comprise hardware (e.g., circuitry, dedicated logic, programmable logic, microcode, etc.), software (such as run on a general purpose computer system or a dedicated machine), or a combination of both. In one embodiment, the process 700 is performed by systems 100 of FIG. 1.

Referring to FIG. 6, processing logic begins with processing logic creating a combined atlas (processing block 702). In one embodiment, the combined atlas is a CT atlas having ultrasound data drawn onto it, so that every position in the CT atlas has a corresponding ultrasound intensity. Alternatively, the combined atlas is an ultrasound atlas having corresponding CT data drawn onto it.

Next, processing logic obtains a CT image of the patient prior to treatment for use in treatment planning (processing block 704) and stores the CT image and the combined atlas in a database.

In one embodiment, processing logic performs blocks 702 through 706 during treatment planning.

At processing block 708, processing logic obtains an ultrasound image of the patient during treatment delivery.

At processing block 710, processing logic retrieves the combined atlas and the pre-operative CT image of the patient from the database.

Further, processing logic registers the pre-operative CT image of the patient with the intra-operative ultrasound image of the patient by first performing a deformable registration of the ultrasound image with the combined atlas using the ultrasound data on the atlas (processing block 712), and then performing a deformable registration of the combined atlas with the CT image using the CT data on the atlas (processing block 714).

In one embodiment, processing logic performs blocks 708 through 714 during treatment delivery.

Figure 7:
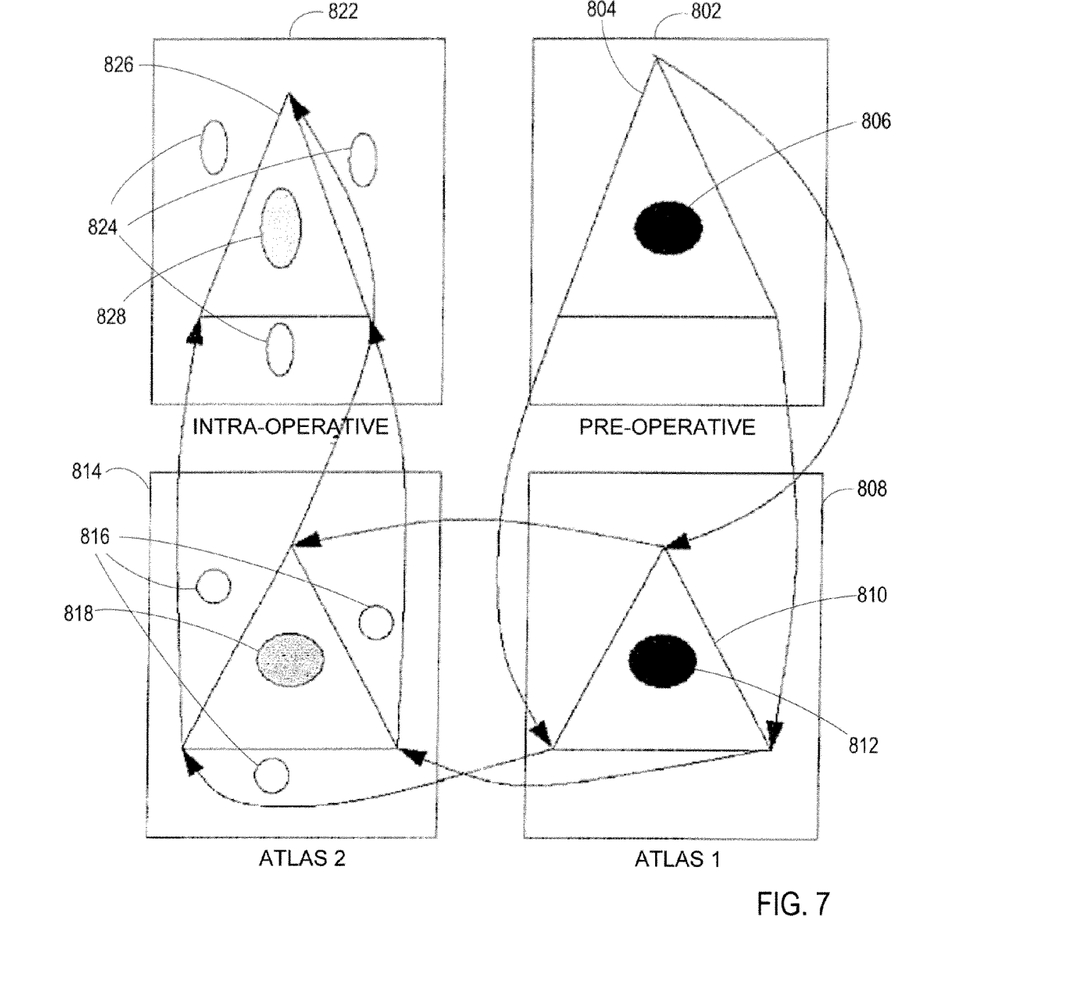
FIG. 7 illustrates exemplary images used in one embodiment of a deformable registration process.

FIG. 7 illustrates exemplary images used in one embodiment of a deformable registration process.

Referring to FIG. 7, image 802 is a pre-operative CT image that contains an anatomical structure 806. Triangle 804 represents the shape of the body of the current patient.

Image 808 is a CT atlas that contains an anatomical structure 812. As discussed above, the CT atlas may be a pre-existing CT image of this or some other patient. Because the patient and/or the patient position is different from the one associated with the CT image 802, triangle 810 differs from triangle 804. Curved lines with arrows illustrate deformation of the CT atlas 808 to match data on the CT image 802.

Atlas 814 represents the CT atlas 808 with corresponding ultrasound information drawn onto it. As shown, atlases 808 and 814 include common data (anatomical structures 812 and 818), as well as some ultrasound-specific data that is not present in the atlas 808 (anatomical structures 816). Curved lines with arrows from the atlas 808 to the atlas 814 illustrate mapping of data between the two atlases.

It should be noted that the atlas 808 is shown for illustration only and may not be needed in the registration process. That is, the CT image 802 may be registered directly with the atlas 814.

Image 822 is an intra-operative ultrasound image that has the same anatomical structures 828 and 824 as the anatomical structures 818 and 816 in atlas 814. The shape of the body of the patient is represented by triangle 826. Curved lines with arrows from the atlas 814 to the ultrasound image 822 illustrate deformation of the image 822 to match data on the atlas 814. The resulting changes on the ultrasound image 822 indicate changes in the patient position and orientation as compared to the patient position and orientation reflected on the pre-operative CT image 802.

In the foregoing specification, embodiments of the invention have been described with reference to specific exemplary embodiments thereof. It will, however, be evident that various modifications and changes may be made thereto without departing from the broader spirit and scope of the present embodiments as set forth in the claims. The specification and drawings are, accordingly, to be regarded in an illustrative rather than a restrictive sense.

What is claimed is:

1. A computer-implemented method comprising:
obtaining a first image using a first imaging modality and a second image using a second imaging modality, wherein the first and second imaging modalities are of different types;
registering a first image atlas of the first imaging modality with a second image atlas of the second imaging modality to generate an atlas registration result; and
registering, by a processing device, the first image with the second image using the atlas registration result.

2. The method of claim 1 wherein the first and second imaging modalities include a pre-operative imaging modality and an intra-operative imaging modality.

3. The method of claim 1 wherein one of the first and second images is an ultrasound (US) image, and the other one of the first and second images is a computed tomography (CT) image.

4. The method of claim 1 wherein one of the first and second images is a magnetic resonance (MR) image.

5. The method of claim 1 wherein one of the first and second images is a positron emission tomography (PET) image.

6. The method of claim 1 wherein each of the first and second images is a three-dimensional (3D) image.

7. The method of claim 1 further comprising tracking a patient based on registering the first image with the second image.

8. The method of claim 1 wherein at least one of the first image atlas and the second image atlas comprises a pre-existing image of an arbitrary patient having substantially normal anatomy in terms of relative position and shape of structure.

9. The method of claim 1 wherein at least one of the first image atlas and the second image atlas comprises an averaged image of multiple arbitrary patients.

10. An apparatus, comprising:
an imaging system to provide a first image using a first imaging modality; and
a patient tracking module comprising processing logic to registering a first image atlas of the first imaging modality with a second image atlas of a second imaging modality to generate an atlas registration result, the processing logic further to register the first image with a second image, obtained using a second imaging modality, using the atlas registration result, wherein the first and second imaging modalities are of different types.

11. The apparatus of claim 10 wherein the first and second imaging modalities include a pre-operative imaging modality and an intra-operative imaging modality.

12. The apparatus of claim 10 wherein one of the first and second images is an ultrasound (US) image, and the other one of the first and second images is a computed tomography (CT) image.

13. The apparatus of claim 10 wherein the patient tracking module is to track a patient based on registering the first image with the second image.

14. A non-transitory machine-readable medium containing instructions which, when executed by a processing device, cause the processing device to perform operations comprising:
obtaining a first image using a first imaging modality and a second image using a second imaging modality, wherein the first and second imaging modalities are of different types;
registering a first image atlas of the first imaging modality with a second image atlas of the second imaging modality to generate an atlas registration result; and
registering, by the processing device, the first image with the second image using the atlas registration result.

15. The machine-readable medium of claim 14 wherein the first and second imaging modalities comprise a pre-operative imaging modality and an intra-operative imaging modality.

16. The machine-readable medium of claim 14 wherein one of the first and second images is an ultrasound (US) image, and the other one of the first and second images is a computed tomography (CT) image.

* * * * *